(12) United States Patent
Molaei (10) Patent No.: US 7,875,070 B2
(45) Date of Patent: Jan. 25, 2011

(54) AVOIDING STRESS-INDUCED MARTENSITIC TRANSFORMATION IN NICKEL TITANIUM ALLOYS USED IN MEDICAL DEVICES

(75) Inventor: Masoud Molaei, Fremont, CA (US)

(73) Assignee: Abbott Laboratories, Abbott Park, IL (US)

( * ) Notice: Subject to any disclaimer, the term of this patent is extended or adjusted under 35 U.S.C. 154(b) by 438 days.

(21) Appl. No.: 11/652,053

(22) Filed: Jan. 11, 2007

(65) Prior Publication Data

US 2007/0162105 A1 Jul. 12, 2007

Related U.S. Application Data

(62) Division of application No. 09/954,557, filed on Sep. 17, 2001, now Pat. No. 7,175,655.

(51) Int. Cl.
*A61F 2/016* (2006.01)
*A61B 17/00* (2006.01)

(52) U.S. Cl. ...................... 623/1.18; 606/194

(58) Field of Classification Search .......... 623/1.11, 623/1.12, 1.15, 1.18, 1.19, 1.2, 1.22; 606/108, 606/191, 194, 195, 198
See application file for complete search history.

(56) References Cited

U.S. PATENT DOCUMENTS

| | | | |
|---|---|---|---|
| 4,505,767 A | 3/1985 | Quin | |
| 4,580,568 A | 4/1986 | Gianturco | |
| 4,665,906 A | 5/1987 | Jervis | |
| 4,856,516 A | 8/1989 | Hillstead | |
| 4,881,981 A | 11/1989 | Thoma et al. | |
| 4,925,445 A | 5/1990 | Sakamoto et al. | |
| 5,067,957 A | 11/1991 | Jervis | |
| 5,092,877 A | 3/1992 | Pinchuk | |
| 5,190,546 A | 3/1993 | Jervis | |
| 5,292,331 A | 3/1994 | Boneau | |
| 5,350,419 A | 9/1994 | Bendel et al. | |
| 5,458,615 A | 10/1995 | Klemm et al. | |
| 5,486,183 A | 1/1996 | Middleman et al. | |
| 5,514,154 A | 5/1996 | Lau et al. | |

(Continued)

FOREIGN PATENT DOCUMENTS

WO  WO 03/028796  4/2003

OTHER PUBLICATIONS

Scott M. Russell et al., *Improved NiTi Alloys For Medical Applications*, Proceedings of the Second International Conference on Shape Memory and Superelastic Technologies, 429-436 (1997).

(Continued)

*Primary Examiner*—Vy Q Bui
(74) *Attorney, Agent, or Firm*—Workman Nydegger (57) ABSTRACT

A process for assembling a medical device made from a nickel-titanium alloy for use in a mammalian body while avoiding the formation of stress-induced martensite and a medical device used in combination with a delivery system for deployment into the mammalian body are disclosed. By heating the nickel-titanium alloy of the medical device to a temperature above $M_d$, and deforming and installing the device into a delivery system or holding capsule, it is possible to avoid the formation of stress-induced martensite in the stent, which stays in the austenitic phase throughout.

15 Claims, 4 Drawing Sheets

U.S. PATENT DOCUMENTS

| | | | |
|---|---|---|---|
| 5,569,295 | A | 10/1996 | Lam |
| 5,597,378 | A | 1/1997 | Jervis |
| 5,632,746 | A | 5/1997 | Middleman et al. |
| 5,637,089 | A | 6/1997 | Abrams et al. |
| 5,643,312 | A | 7/1997 | Fischell et al. |
| 5,720,754 | A | 2/1998 | Middleman et al. |
| 5,843,244 | A | 12/1998 | Pelton et al. |
| 5,885,381 | A | 3/1999 | Mitose et al. |
| 5,891,191 | A | 4/1999 | Stinson |
| 5,907,893 | A | 6/1999 | Zadno-Azizi et al. |
| 5,927,345 | A | 7/1999 | Samson |
| 5,931,819 | A | 8/1999 | Fariabi |
| 5,976,153 | A | 11/1999 | Fischell et al. |
| 6,004,330 | A | 12/1999 | Middleman et al. |
| 6,051,021 | A | 4/2000 | Frid |
| 6,059,810 | A | 5/2000 | Brown et al. |
| 6,086,610 | A | 7/2000 | Duerig et al. |
| 6,129,755 | A | 10/2000 | Mathis et al. |
| 6,149,742 | A | 11/2000 | Carpenter et al. |
| 6,171,334 | B1 | 1/2001 | Cox |
| 6,190,406 | B1 | 2/2001 | Duerig et al. |
| 6,217,567 | B1 | 4/2001 | Zadno-Azizi et al. |
| 6,254,550 | B1 | 7/2001 | McNamara et al. |
| 6,287,292 | B1 | 9/2001 | Fariabi |
| 6,306,141 | B1 | 10/2001 | Jervis |
| 6,323,459 | B1 | 11/2001 | Maynard |
| 6,626,937 | B1 * | 9/2003 | Cox .......................... 623/1.18 |
| 7,175,655 | B1 | 2/2007 | Molaei |

OTHER PUBLICATIONS

U.S. Appl. No. 09/954,557, Mail Date Nov. 27, 2002, Office Action.
U.S. Appl. No. 09/954,557, Mail Date Mar. 11, 2003, Office Action.
U.S. Appl. No. 09/954,557, Mail Date Sep. 8, 2003, Office Action.
U.S. Appl. No. 09/954,557, Mail Date Nov. 24, 2003, Office Action.
U.S. Appl. No. 09/954,557, Mail Date Dec. 3, 2004, Office Action.
U.S. Appl. No. 09/954,557, Mail Date Jul. 7, 2005, Office Action.
U.S. Appl. No. 09/954,557, Mail Date Sep. 28, 2005, Office Action.
U.S. Appl. No. 09/954,557, Mail Date Feb. 8, 2006, Office Action.
U.S. Appl. No. 09/954,557, Mail Date Sep. 27, 2006, Notice of Allowance.
U.S. Appl. No. 09/954,557, Mail Date Jan. 24, 2007, Issue Notification.
Duerig, T.W. et al., *Ti-Ni Shape Memory Alloys,* Advanced Materials, 1035-1048. ASM, Int'l (1994).
Duerig, T.W. et al., *An Engineer's Perspective of Pseudoelasticity,* Engineering Aspects of Shape Memory Alloys, pp. 369-393 (1990).
Pelton, A.R. et al. "Optimization of Processing and Properties of Medical Grade Nitinol Wire," pp. 107-118 Minimally Invasive Therapy and Allied Technologies (2000).
Schetky, L. McDonald Shape Memory Alloys, Scientific American, pp. 74-82 (Nov. 1979).
Minimally Invasive Therapy & Allied Technologies-Offical Journal of the Society for Minimally Invasive Therapy-Edited by John Wickman and Gerhard F. Buess-pp. 106-118 (2000).
Johnson Matthey Nitinol Products, Shaping the Nitinol Industry, Using Nitinol Alloys, p. 1-77 (2004).
Johnson Matthey Nitinol Products, Shaping the Nitinol Industry, Using Nitinol Alloys, p. 1-77 (2004)(upon information and belief, based upon information received from the publisher, this document is a reprint of Hodgson, D.E. et al. "Using Nitinol Alloys," p. 1-38 Shape Memory Applications, Inc. (2000), with a different cover).

* cited by examiner

AVOIDING STRESS-INDUCED MARTENSITIC TRANSFORMATION IN NICKEL TITANIUM ALLOYS USED IN MEDICAL DEVICES

This is a division of application Ser. No. 09/954,557, filed Sep. 17, 2001, now U.S. Pat. No. 7,175,655, which is incorporated herein by reference.

BACKGROUND OF THE INVENTION

This invention relates generally to improvements in methods and apparatus incorporating shape memory alloys, and, more particularly, to the use of nickel-titanium (NiTi) alloys as a medical device or a medical device component deformed in an austenitic state prior to being packed into a tube, catheter or the like, and subsequently deployed into a mammalian body for appropriate medical treatment.

It is well known in the field that both organic and metallic materials are capable of exhibiting shape memory effect. The nickel-titanium alloy known as "nitinol," is an extensively used metal alloy for medical device applications and possesses unique properties under certain conditions. One benefit of applying nitinol to medical devices is that the alloy has tremendous elasticity and useful shape memory characteristics. In terms of its elasticity, nitinol can become highly elastic under certain conditions in that it is able to experience extensive deformation and yet transform back to its original shape. This beneficial attribute of nitinol is known as superelasticity, also commonly referred to as pseudoelasticity. Superelasticity or pseudoelasticity refers to the ability of a material to undergo extremely large elastic deformation. The shape memory properties of nitinol enable it to "remember" a particular shape instilled during a previous heat set operation and to transform back to that shape when desired. Furthermore, nitinol is highly biocompatible, kink resistant, fatigue resistant, and has other beneficial engineering attributes thus making the material particularly useful in medical applications.

In one particular application, nitinol has found use in self-expanding stents. Historically, stents were not self-expanding but rather were expanded and deployed by a balloon catheter. Balloon expanded stents are used in conjunction with balloon angioplasty procedures with the intent to reduce the likelihood of restenosis of a diseased vessel. Stents are also used to support a body lumen, tack-up a flap or dissection in a vessel, or in general where the lumen is weak to add support.

For balloon expandable stents, the stent is positioned over the balloon portion of a catheter and is expanded from a reduced delivery diameter to an enlarged deployment diameter greater than or equal to the inner diameter of the arterial wall by inflating the balloon. Stents of this type are expanded to an enlarged diameter through deformation of the stent, which then engages the vessel wall. Eventual endothelial growth of the vessel wall covers the stent.

Nitinol then found use in self-expanding stents, where deployment was a result of either shape-memory effect or superelasticity in the material rather than by use of a dilatation balloon. The stent once released from its delivery system assumed a pre-set shape in the body lumen. Such self-expanding stents are used to scaffold the inside circumference of a tubular passage such as an esophagus, bile duct, or blood vessel.

The benefits of using a superelastic nitinol material for self-expanding stents are primarily related to its large recoverable strain. The biocompatibility of nickel-titanium is also an attractive benefit for use of this material in stenting applications, because the stent remains in the patient as part of the treatment.

The use of nickel-titanium as a balloon-expandable stent is less common. The balloon-expandable and scaffolding capabilities of such stents are accomplished by setting the austenite finish temperature ($A_f$) at about 55 degrees C. or well above body temperature. The stent is therefore completely martensitic before, during, and after balloon deployment. A significant disadvantage of such a balloon-expandable nitinol stent in its martensitic phase is that martensite is very soft. Therefore, the scaffolding function and hoop strength of the stent are diminished.

As briefly described above, superelasticity or pseudoelasticity, refers to the highly exaggerated elasticity or springback observed in many nickel-titanium alloys deformed above their austenite finish temperature ($A_f$) and below the martensite deformation temperature ($M_d$). Hence, nickel-titanium alloys can deliver over fifteen times the elasticity of a spring steel. The martensite deformation temperature ($M_d$) is defined as the temperature above which martensite cannot be stress-induced. Consequently, nickel-titanium remains in its austenitic phase throughout an entire deformation test above $M_d$.

The shape memory effect characteristic of nitinol is a result of metallurgical phase transformations. Depending on its temperature, the structural properties of nitinol enable it to function in two different states. At the lower temperature range, below a specified transition temperature, the nitinol alloy becomes more flexible and malleable and is said to be in the martensitic state. However, when heated above the specified transition temperature, the nitinol alloy transforms into its predetermined heat set shape in the austenitic state.

The alloy can also undergo a thermoelastic martensitic transformation from an austenitic state to a martensitic state without a change in temperature. This transformation involves two characters, $M_s$ (the temperature at which the transformation begins) and $M_f$ (the temperature at which the transformation finishes). Thus, when a shape memory alloy is at a temperature above $M_s$ (when the austenite state is initially stable), but below $M_d$ (the maximum temperature at which martensite transformation can occur), and is stressed, it begins to elastically deform, and thereafter, at a critical stress, the alloy transforms from austenite to stress-induced martensite. In the case of austenitic transformation, the alloy in the martensitic state undergoes a reverse transformation when it is warmed to a temperature at which the alloy begins to transform back to austenite, referenced by the character, $A_s$, with $A_f$ as the temperature at which the reversion is complete. The martensite is stable at a temperature below $A_s$, and unstable at a temperature above $A_s$ in which the martensite transforms back to austenite and the material assumes its original shape. This shape memory effect is characteristic of nearly all alloys that exhibit thermoelastic martensitic transformation. It is important to recognize, however, that the stress and strain ranges for the effect, in addition to the range of temperatures over which stress-induced martensite occurs, vary significantly depending on the type of alloy used. Various medical devices incorporating the use of shape memory elements have been known for a number of years.

The various medical devices adopting the use of shape memory elements into their design as referenced above essentially rely on the unique structural properties of shape memory alloys in order to achieve their desired effects. In other words, shape memory alloys retain their new shape when cooled to the martensitic state and thereafter deformed;

however, these same shape memory alloys will recover their original shape when warmed to the austenitic state.

Notwithstanding the beneficial effects of shape memory alloys employed in a wide variety of medical applications, disadvantages are also apparent. First, due to the fact that shape memory alloys are typically very composition-sensitive, it can be quite difficult to accurately control their transformation temperatures. Second, as a shape memory alloy undergoes a transformation between the austenitic and martensitic states, there can be a significant lag such that a reversal of the state of a shape memory alloy may result in a temperature set-off of several tens of degrees Celsius. In addition, the use of shape memory alloys in medical devices is expected to be limited due to the difficulties associated with temperature control and the biological limitations of human tissue in its ability to be repeatedly heated and cooled within certain narrow restraints (approximately 0°-60° C. for short periods of time) so as not to sustain any temporary or permanent damage.

What has been needed and heretofore not been used in the engineering of medical devices incorporating shape memory alloy elements is a method and apparatus for avoiding stress-induced martensitic transformation in nickel titanium alloys so that these type of alloys may instead be deformed in the austenitic state prior to their packing within a catheter, tube or the like, and hence avoid the extreme low temperatures normally used to deform such alloys. The present invention satisfies this need and others.

SUMMARY OF THE INVENTION

The present invention is directed to a medical device for use in a mammalian body, the medical device completely lacking stress-induced martensite. The invention is further directed to an apparatus for receiving the medical device in an austenitic state, and for deploying the same within the mammalian body.

In a first exemplary embodiment, the invention relates to a process for deforming a medical device for use in a mammalian body. The process involves the use of a shape memory alloy with an associated martensite deformation temperature ($M_d$), wherein the element includes a restrained shape and a deployed shape. A hollow delivery system, such as a catheter, at least partially contains the medical device including the shape memory alloy element. The shape memory alloy is heated to a temperature at or above $M_d$ where the alloy is at least partially deformed into a restrained shape while in an austenitic state. The medical device is positioned at least partially inside the hollow delivery system to hold the shape-memory alloy in the restrained shape.

In one aspect, the process further includes cooling the medical device inside the hollow delivery system to room temperature. Preferably, the shape memory alloy is in an austenitic state at room temperature of about 22 degrees Celsius (C). The shape memory alloy can embody nickel and titanium. In contemplated embodiments, the medical device formed from the process includes a stent, and the delivery system includes a catheter having structure that accomplishes at least partially deforming the element into a restrained shape without generating stress-induced martensite.

The invention also relates to a medical device and delivery system that includes a shape memory alloy element having a restrained shape and a deployed shape, wherein the shape memory alloy element is deformed at or above $M_d$. A hollow delivery system holds the at least partially deformed shape memory alloy element in its restrained shape. The shape memory alloy does not embody stress-induced martensite from being at least partially deformed into a restrained shape.

In one particular aspect, the shape memory alloy is formed into a tubular member with proximal and distal ends with a restraint secured around the shape memory alloy in its deformed configuration. Also, the shape memory alloy is configured for use within a mammalian body or in close proximity to the mammalian body such that the device is at mammalian body temperature.

In a preferred embodiment, the invention is contemplated to be placed within a mammalian body having a body temperature of about 35 to 40 degrees Celsius (C). The shape memory alloy has an austenite start temperature ($A_s$) an austenite finish temperature ($A_f$), and a martensite deformation temperature ($M_d$). The shape memory alloy preferably includes an $M_d$ of about 50 degrees C. above $A_f$ which is set at about 10 degrees C. Also, the shape memory alloy is at room temperature inside the hollow delivery system prior to being deployed into the mammalian body. The shape memory alloy is in an austenite state at room temperature of about 22 degrees C.

The invention further relates to a process for assembling a medical device for use in a mammalian body. The process involves the use of a shape memory alloy with a martensite deformation temperature ($M_d$), wherein the element includes a restrained shape and a deployed shape. A hollow holding capsule at least partially contains the medical device including the shape memory alloy element. The shape memory alloy is heated to a temperature at or above $M_d$ where the alloy is at least partially deformed into a restrained shape while in an austenitic state. The medical device is positioned at least partially inside the hollow holding capsule to hold the shape-memory alloy in the restrained shape.

In one embodiment, the heating of the nitinol is performed by a light source such as a flood light positioned inside an isothermal temperature-controlled chamber. The heating of the nitinol may also be performed by a heated fluid, infrared light, ultrasonic vibration, or by a current source connected to the shape memory alloy element.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

The present invention is directed to a process for avoiding formation of stress-induced martensite in nickel-titanium alloys used in medical devices and an apparatus incorporating the steps from this process to deform a device for use in the mammalian body. For illustration purposes, the following exemplary embodiments are limited to intraluminal stents. However, it is recognized that the present invention is not limited to such applications and rather may be used in various other medical devices (e.g., guide wires) where the same principles are applicable.

Figure 1:
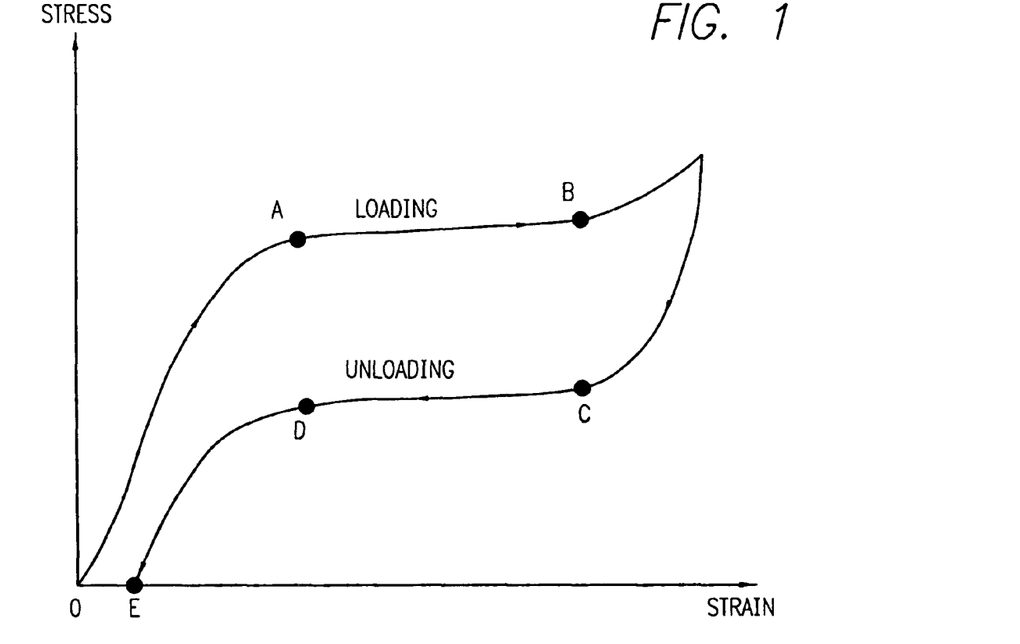
FIG. 1 is a stress-strain hysteresis curve for a nickel-titanium superelastic alloy.

As shown in FIG. 1 is a stress-strain hysteresis curve for a binary nickel-titanium alloy demonstrating the loading and unloading of the metal alloy. A more detailed discussion of nickel-titanium behavior may be found in T. W. Duerig, A. R. Pelton, "Ti—Ni Shape Memory Alloys, Materials Properties Handbook Titanium Alloys," pp. 1035-1048, ASM International (1994), the contents of which are incorporated herein by reference. Additional industry literature by D. E. Hodgson, J. W. Brown, "Using Nitinol Alloys," pp. 1-38, Shape Memory Applications, Inc. (2000), provides an overview of the phenomenon of the shape memory effect exhibited by nitinol, the contents of which are incorporated herein by reference. With regard to the use of nitinol for medical device applications, particularly for guide-wire applications, the article by A. R. Pelton et al., "Optimisation of Processing and Properties of Medical Grade Nitinol Wire," pp. 107-118, Minimally Invasive Therapy & Allied Technologies (2000), provides an in-depth discussion in this area, the contents of which are incorporated herein by reference.

As illustrated in FIG. 1, the curve is also generally known as a superelastic curve which is characterized by areas of nearly constant stress during loading and unloading of the metal alloy. The line segment A-B, as depicted in FIG. 1, is the constant loading stress and is referred to as the loading plateau stress while the line segment C-D is the constant unloading stress and is referred to as the unloading plateau stress. The permanent set of the material in which the strain is not recoverable is represented by the distance between point E and the origin O of FIG. 1.

The stress-strain hysteresis curve, as depicted in FIG. 1, is for a nickel-titanium alloy tested above its austenitic finish temperature ($A_f$) but below its martensite deformation temperature ($M_d$). The austenite finish temperature ($A_f$) is the temperature at which the nickel-titanium alloy completely converts to austenite. The onset of superelasticity occurs in the narrow temperature range just above $A_f$. The superelasticity performance of the nickel-titanium alloy steadily declines while approaching the martensite deformation temperature ($M_d$), at which point stress-induced martensite no longer appears and all superelasticity is hence eliminated.

The curve depicted in FIG. 1 represents the temperature range just above $A_f$ where superelasticity does occur. In such case, as the material is stressed, the curve is represented by sloped line O-A in which the material is completely austenitic. The transformation from austenite to stress-induced martensite (SIM) occurs at generally labeled point A indicated in FIG. 1. At a particular theoretical stress level, maintaining constant stress completely converts the austenite to stress-induced martensite in the nickel-titanium alloy, as represented by line segment A-B. Further application of stress beyond point B creates elastic deformation in the stress-induced martensite. A continuous application of stress leads to elastic deformation, represented by an upward slope, then plastic deformation, which is not shown in FIG. 1, in the stress-induced martensite.

The slope of the curve depicted in FIG. 1 reverses from beyond point B, dropping down to point C, as a result of the release of stress. Generally, at approximately point C represents the initial conversion of stress-induced martensite back to austenite. At a certain stress level, as represented by line segment C-D, the material converts entirely from the stress-induced martensitic phase to the austenitic phase. Further release of the applied stress is represented by sloped line D-E which in turn represents the elastic deformation of the austenitic phase. As previously mentioned above, the permanent set of unrecoverable strain in the material is represented by strain E.

Figure 2:
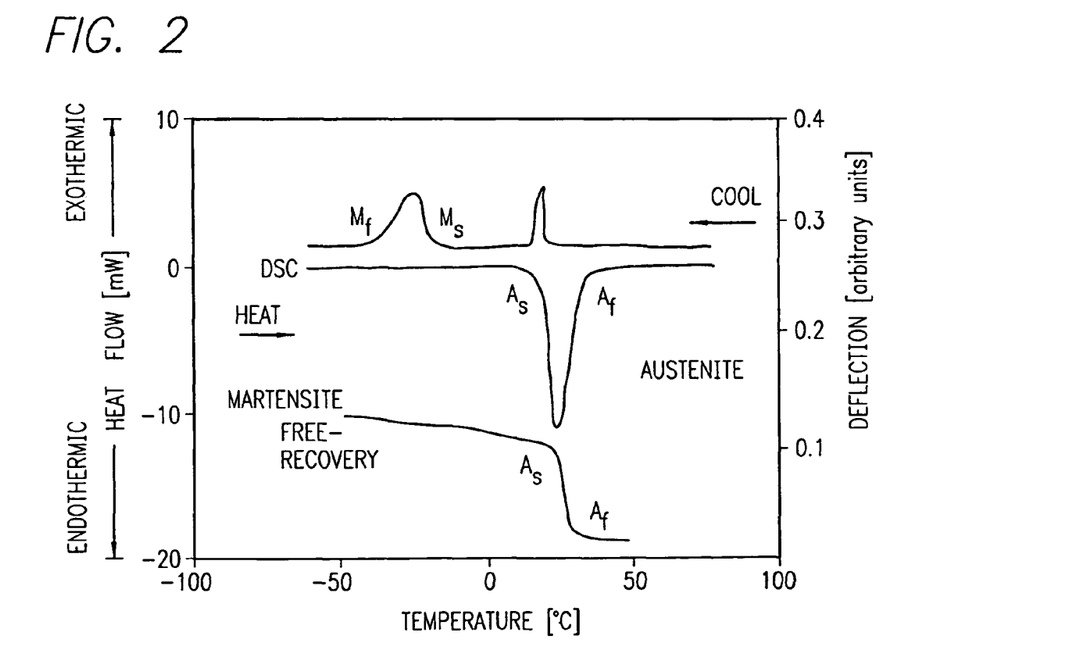
FIG. 2 is a schematic depicting the comparison between a Differential Scanning Calorimetry (DSC) thermogram and instrumented free-recovery measurements from the same processed nitinol wire.

With reference to FIG. 2, there is shown a schematic depicting the comparison between differential scanning calorimetry (DSC) and free recovery techniques in measuring the amount of heat absorbed and released during the martensitic and austenitic transformations, and the deflection recovery of the nitinol wire only during heating, respectively. The transformation temperatures are represented by the following characters, including $M_s$, $M_f$, $A_s$, and $A_f$. In particular, the DSC technique measures the amount of heat released and absorbed during the martensitic (exothermic) and austenitic (endothermic) transformations. However, the simplest and perhaps most useful method of measuring $A_f$ is through the free recovery technique. Measurement through the free recovery technique requires the application of three basic steps which collectively simulate a shape-memory cycle. These specific steps are set forth in the above mentioned article entitled, "Optimisation of Processing and Properties of Medical Grade Nitinol Wire," the contents of which are incorporated herein by reference.

The aforementioned references to FIGS. 1 and 2 serve to provide a brief overview of the unique mechanical properties of the shape memory alloy, nitinol, which relates to the present invention.

The present invention is directed to a process for assembling a medical device for use in a mammalian body that includes providing a shape memory alloy element having a martensite deformation temperature ($M_d$), wherein the element includes a restrained shape and a deployed shape. A hollow delivery system at least partially contains the medical device including the shape memory alloy element. The shape memory alloy element is heated to a temperature at or above $M_d$ and is subsequently at least partially deformed into the restrained shape. The medical device including the element is positioned at least partially inside the hollow delivery system to hold the element in the restrained shape. While inside the hollow delivery system, the medical device is cooled down to room temperature prior to deploying in the mammalian body.

Figure 3:
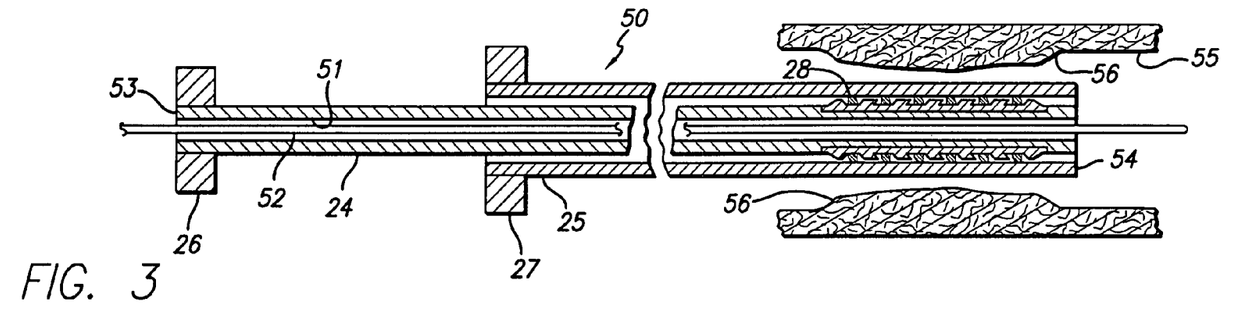
FIG. 3 is a schematic view of an over-the-wire catheter-delivery system in which the stent is being positioned at a narrowed portion of the vessel wall.
Figure 4:
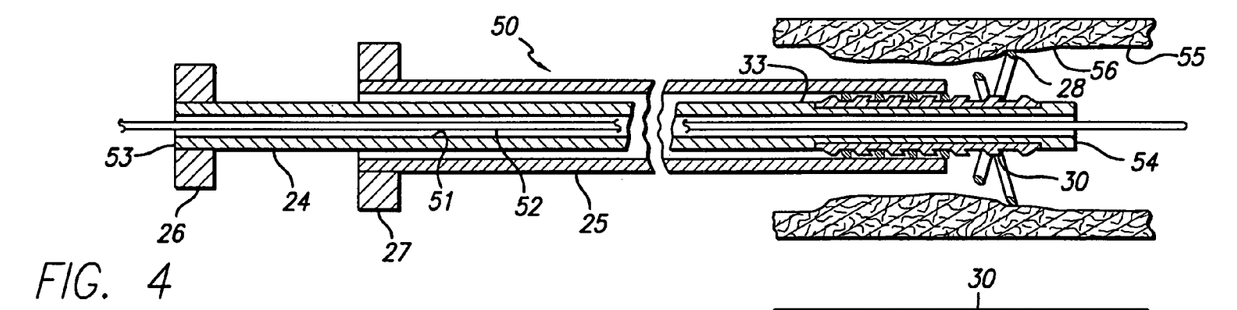
FIG. 4 is a schematic view depicting the over-the-wire catheter-delivery system of FIG. 3 in which the outer member is being withdrawn proximally so that the stent can self-expand radially outwardly into contact with the vessel wall.
Figure 5:
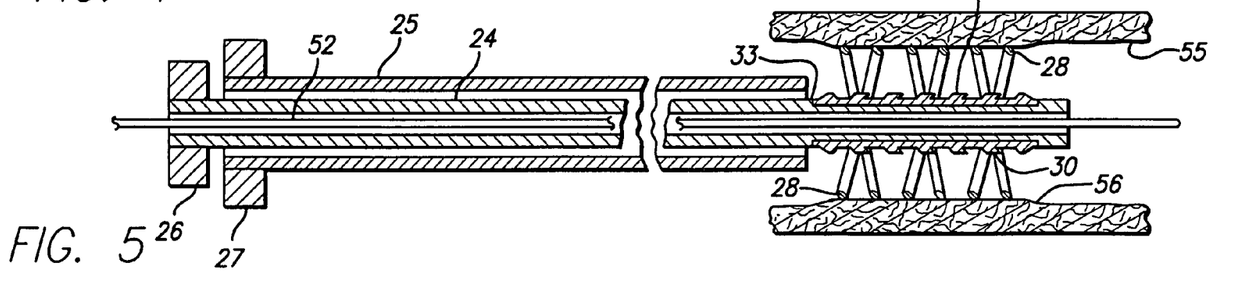
FIG. 5 is a schematic view depicting the stent of FIGS. 3 and 4 being implanted and contacting the vessel wall.

In one exemplary application, a nitinol alloy is used to fabricate a stent. FIG. 3 is a schematic view of an over-the-wire catheter-delivery system in which the stent is being positioned at a narrowed portion of the vessel wall. Other delivery systems, such as the rapid exchange stent delivery systems, may be used without departing from the scope of the present invention. The catheter assembly 50 of FIG. 3 is used to implant the self-expanding stent in a body lumen using an over-the-wire or rapid-exchange catheter configuration. In one preferred embodiment, as depicted in FIGS. 3-5, an over-the-wire catheter 50 has a guide wire lumen 51 which extends through the catheter and is configured to receive guide wire 52. In order to implant a self-expanding stent 28, guide wire 52 is positioned in a patient's body lumen, at vessel wall 55, and typically guide wire 52 extends past a stenosed region 56. A distal end 54 of over-the-wire catheter 50 is threaded over the proximal end of the guide wire which is outside the patient (not shown) and catheter 50 is advanced along the guide wire until distal end 54 of catheter 50 is positioned within stenosed region 56.

As depicted in FIGS. 4 and 5, self-expanding stent 28 is implanted in stenosed region 56 by moving an outer member 25 in a proximal direction while simultaneously moving an inner member 24 in a distal direction. The stent 28 will not slide or move axially on an outer surface 33 since the open lattice structure is filled in with attachment projections 30. As portions of self-expanding stent 28 are no longer contained by outer member 24, it will expand radially outwardly into contact with vessel wall 55 in the area of stenosed region 56. When fully deployed and implanted, as shown in FIG. 5, stent 28 will support and hold open stenosed region 56 so that blood flow is not restricted. Attachment projections 30 do not inhibit the stent 28 from self-expanding radially outwardly, they only impede axial movement of the stent. After stent 28 is implanted and contacts stenosed region 56, over-the-wire catheter 50 is withdrawn from the patient's vascular system.

The aforementioned delivery system in FIGS. 3-5 is merely intended to be an example of a delivery system that may be used in combination with the present invention, hence is not limited to solely that type of delivery system. Thus, nearly any type of delivery system may be contemplated for use with the present invention.

A standard superelastic nitinol (55.3-56.3 wt. % Ni) is contemplated to be used. Some strengthening elements such as Cr may also be added. Tensile testing of the type of nitinol used in fabricating the stents of the present invention establishes that the nitinol is at or above $M_d$ when the test sample exhibits large amounts of permanent set. Due to such plastic deformation, the device is contemplated to be designed in a manner to compensate for the deformation so that the ultimate desired size and shape of the device is achieved.

In a preferred embodiment, an electric light is used as a heat source to raise the temperature of the nitinol stent above $M_d$. The light is preferably of the type of a regular flood light having sufficient voltage to heat the nitinol stent. Other types of lights may be used rather than just a flood light so long as sufficient voltage is used from one or more lights to heat the nitinol stent with approximately the same intensity as a flood light.

Figure 8:
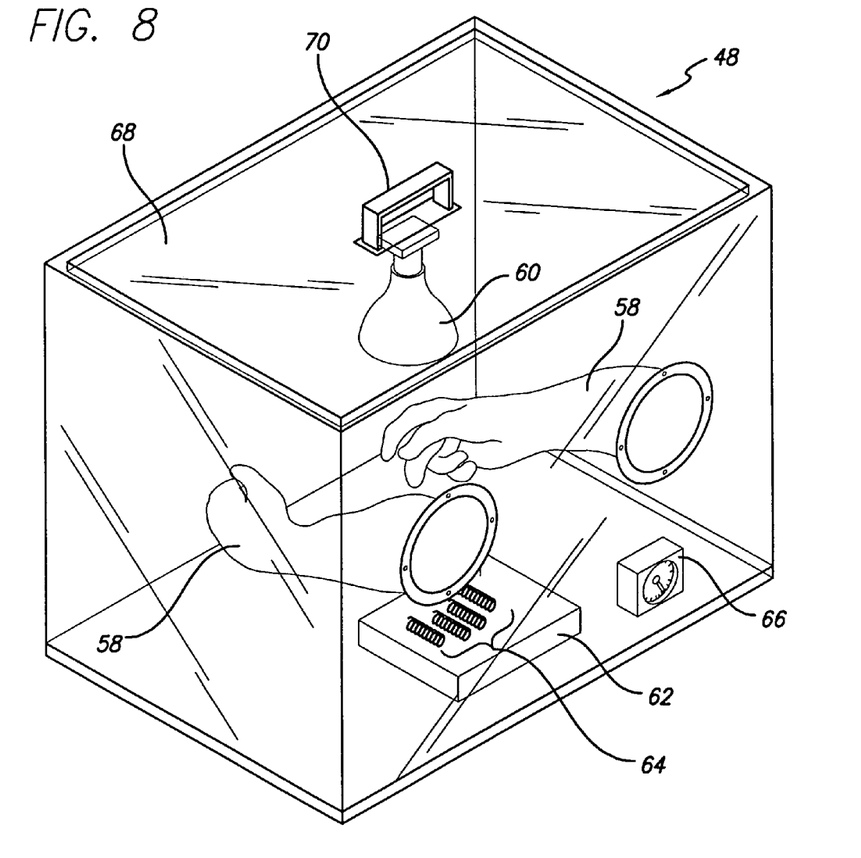
FIG. 8 is a perspective view of a preferred embodiment apparatus for heating and deforming the nitinol stent with a light source positioned inside an isothermal, temperature-controlled, transparent chamber.

As shown in FIG. 8, the light source 60 is preferably set up in a transparent chamber 48 with gloves 58 attached on each side of the chamber 48 to maneuver the nitinol stents 64 within the chamber 48 during the deformation process. The nitinol stents 64 may set on an elevated work platform 62 to ease handling of the stents 64. A thermometer 66 may be placed inside the chamber 48 to monitor the temperature. The inside of the chamber 48 may be accessed by lifting the top lid 68 of the chamber 48 by the handle 70. The transparent chamber 48 is an ideal isothermal temperature-controlled environment for deforming the nitinol stent 64 at a temperature above $M_d$.

Figure 6:
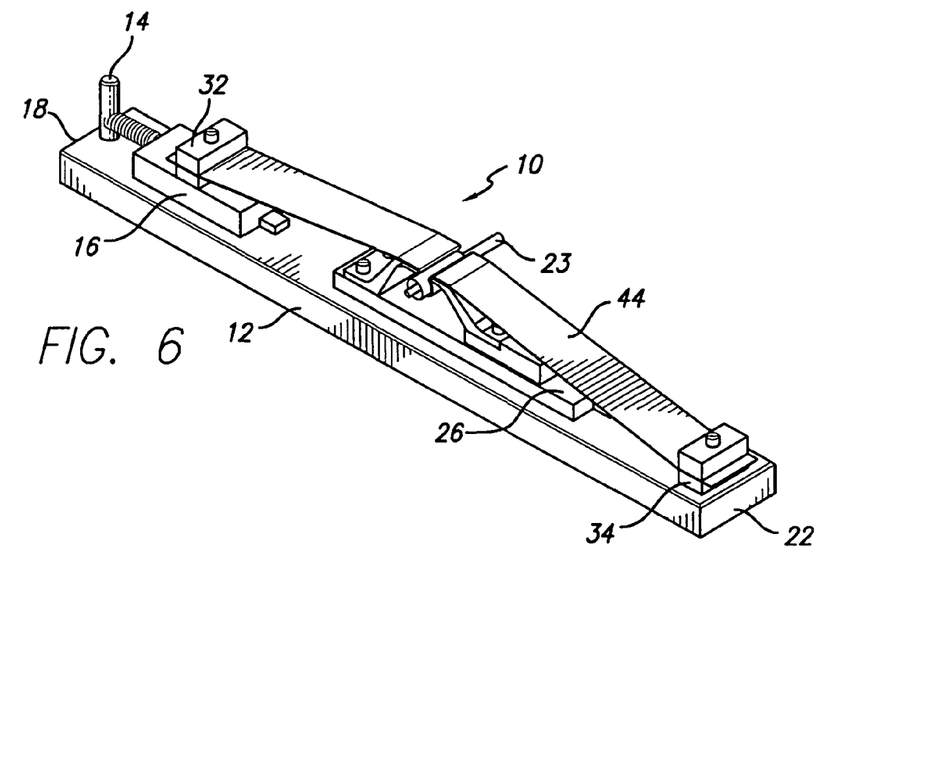
FIG. 6 is a perspective view of a preferred embodiment apparatus for collapsing self-expanding nitinol stents and loading the stents into a delivery catheter.

After heating the nitinol stent 64 inside the isothermal temperature-controlled chamber 48 (FIG. 8), the stent 64 is immediately removed from the chamber 48 and placed into a stent crimping device 25, as shown in FIG. 6, for loading into a delivery system where it will then cool down to room temperature. The procedure can be performed efficiently prior to the stent cooling down to a temperature below $M_d$. FIG. 6 is an apparatus for collapsing or crimping self-expanding nitinol stents and loading the stents into a delivery catheter. The present invention employs the use of this particular device which can repeatedly provide a uniform and tight collapse of the stent to ensure the low profile diameter of the stent for placement into a smaller diameter delivery catheter at which time there is deformation of the stent at or above $M_d$.

Figure 7:
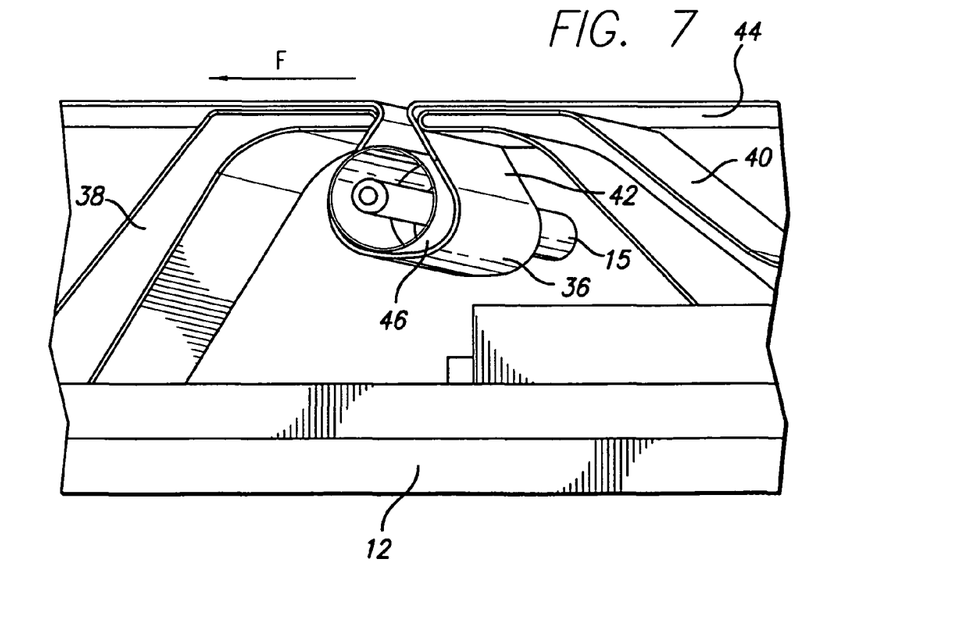
FIG. 7 is a close-up, perspective view of the preferred embodiment apparatus of FIG. 6.

With further reference to FIGS. 6 and 7, the various parts of the device, such as a base piece 26 and a belt piece 44 are connected such that mounts 32 and 34, having the belt end portions clamped therein, are attached to the elongate base plate 12. The first mount 32, may be spaced apart from the second mount 34 and attached over a pin 14 on a first sliding plate 16 situated at one end, preferably a first end 18, of the elongate base plate 12. The second mount 34 may be attached to a second edge 22, of the elongate base plate 12. A belt mid-portion 36 may loosely rest upon first and second jaw blocks 38 and 40. The belt mid-portion 36, being loosely mounted to the base piece 26 may form a belt loop 42 between the first and second jaw blocks 38 and 40 for receiving a stent 46 to be collapsed. The belt loop 42 is formed from the gravitational slag created when the belt 44 is loosely laid to rest upon the jaw blocks 38 and 40, the more slag that is available on the belt the bigger the loop 42 may be. In general, the loop 42 should initially be of generous size, forming a loop having a circumferential size large enough to easily receive a stent 46 in an expanded first diameter.

Referring to FIG. 7, an enlarged view of the collapsing machine is provided, depicting the first and second jaw blocks 38 and 40 with the belt loop 42, formed from the belt 44 mid-section 36, having a stent 46 disposed therein. When the flexible belt 44 is pulled taut in a predetermined direction represented by arrow F, the size of loop 42 is uniformly decreased and a radially collapsing force is introduced upon the outer circumference of the stent 46 causing it to collapse upon a first section of a support pin 15. As the belt is pulled taut to a predetermined tightness, a given amount of radial force is provided to collapse the stent 46 upon the support pin 15 until it is well collapsed thereon.

Figure 9:
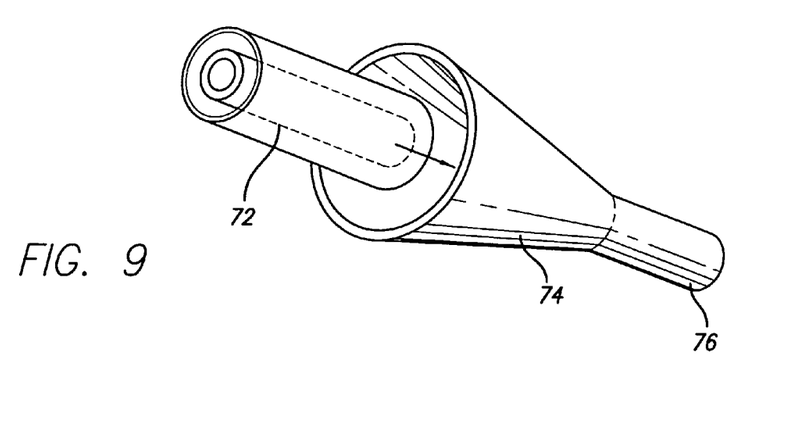
FIG. 9 is a close-up, perspective view of a preferred embodiment apparatus for maintaining the deformed shape of an austenitic nitinol stent.

Alternatively, if the deformed nitinol stent is not ready for loading into the delivery system and subsequent deployment in the mammalian body, it can be held in the interim inside a holding capsule 76, as shown in FIG. 9, preferably constructed from a funnel 74 to maintain the position of the deformed stent 72. In order to maintain the deformed shape of the nitinol stent 72, the diameter of the funnel 74 device is the same as or slightly larger than the deformed nitinol stent 72. The nitinol stent 72 remains in the holding capsule 76 until positioned or otherwise aligned inside a catheter restraint for deployment in the mammalian body. Once the nitinol stent is loaded into the delivery catheter, the stent-catheter assembly can be sterilized according to processes known in the art before deployment in the mammalian body.

In an alternative embodiment, a hot water bath is used as a heat source to raise the temperature of the nitinol stent above $M_d$. The heating of the nitinol stent is, preferably performed in a controlled environment such as in a glass-enclosed chamber 48 (FIG. 8) containing the water bath assembly. An exhaust fan may be installed inside the chamber to help with evaporation. Any type of water may be used in the heating of the nitinol stent such as tap, distilled water or the like. Once the bath has reached the desired temperature, the nitinol stent is placed inside the bath and subsequently deformed.

After heating and deforming the nitinol stent in the hot water bath assembly, the stent is immediately removed from the container and glass chamber 48 (FIG. 8) and thereafter loaded into a delivery system to cool down to room temperature. Any excess moisture remaining on the nitinol stent after being removed from the hot water bath may be removed by briefly placing the stent into a warm alcohol bath located outside of the glass-enclosed chamber 48 under a fume hood, and then loaded into a delivery system to cool down to room temperature prior to deployment in the mammalian body. Alternatively, a flow of warm air directed to the nitinol stent can be used to evaporate any excess moisture from the nitinol stent until being further positioned or otherwise aligned inside a catheter restraint to cool down to room temperature prior to deployment in the mammalian body. The same procedures discussed above apply regarding the alternative placement of the nitinol stent 72 into a holding capsule 76 (FIG. 9) made from a funnel 74 if the stent 72 is not ready to be positioned inside a catheter restraint for deployment in the mammalian body. The stent-catheter assembly is sterilized according to processes known in the art before deployment in the mammalian body.

In another alternative embodiment, the nitinol stent is exposed to ultrasonic treatment to heat the nitinol to a temperature above $M_d$. A fluid medium containing the stent may be vibrated at ultrasonic frequencies to generate heat in the nitinol stent.

In yet another alternative embodiment, the nitinol stent is exposed to infrared light to heat the nitinol to a temperature above $M_d$. The use of infrared light as a heat source in raising the temperature of the nitinol stent above $M_d$ applies the same general principle as the use of a floodlight in heating the nitinol stent. Accordingly, the same procedures set forth above in the preferred embodiment apply to infrared light as a heat source.

In still another alternative embodiment, the nitinol stent is exposed to an electric current to heat the nitinol to a temperature above $M_d$. A DC current is applied to the stent in order to use the internal resistance of the nitinol material to generate heat. A DC power supply can be used and set to a certain voltage in order to ensure that the nitinol stent is heated above $M_d$.

In a further alternative embodiment, the nitinol stent is exposed to a warm plate to heat the nitinol to a temperature above $M_d$ through conduction. The nitinol stent is rolled in a continuous movement across the surface of the warm plate to sufficiently heat while being deformed.

While several particular forms of the invention have been illustrated and described, it will also be apparent that various modifications can be made without departing from the spirit and scope of the invention. Accordingly, it is not intended that the invention be limited, except as by the appended claims.

What is claimed is:

1. A process for deforming a medical device including a shape memory alloy element having a martensite deformation temperature ($M_d$), wherein the element includes a restrained shape and a deployed shape for use in a mammalian body, comprising:
   heating the shape memory alloy element to a temperature at or above $M_d$, wherein $M_d$ is greater than a body temperature of the mammalian body;
   at least partially deforming the heated element into the restrained shape; and
   applying a force to maintain the element in the restrained shape.

2. The process of claim 1, further comprising positioning the medical device including the element at least partially inside a hollow delivery system to hold the element in the restrained shape.

3. The process of claim 2, further including cooling the medical device inside the hollow delivery system to room temperature.

4. The process of claim 1, wherein the shape memory alloy is in an austenitic state at room temperature of about 22 degrees C.

5. The process of claim 1, wherein the shape memory alloy includes nickel and titanium.

6. The process of claim 1, wherein the medical device includes a stent.

7. The process of claim 1, wherein the step of at least partially deforming the heated element into a restrained shape does not generate stress-induced martensite.

8. The process of claim 1, wherein the hollow delivery system includes a catheter.

9. The process for deforming a medical device of claim 1, wherein the heating is performed by a light source.

10. The process for deforming a medical device of claim 1, wherein the heating is performed by heated fluid.

11. The process for deforming a medical device of claim 1, wherein the heating is performed by ultrasonic vibration.

12. The process for deforming a medical device of claim 1, wherein the heating is performed by a current source connected to the shape memory alloy element.

13. The process for deforming a medical device of claim 1, wherein the heating is through rolling nitinol stent on a warm plate.

14. The process for deforming a medical device of claim 1, wherein $M_d$ is about 50 degrees C. or more than an austenite finish temperature ($A_f$) of the shape memory element.

15. The process for deforming a medical device of claim 1, further comprising self-expanding the shape memory element from the restrained shape to the deployed shape within the mammalian body.

* * * * *